(12) United States Patent
Featonby et al.

(10) Patent No.: US 9,869,647 B2
(45) Date of Patent: Jan. 16, 2018

(54) SCANNING METHOD

(71) Applicant: JOHNSON MATTHEY PUBLIC LIMITED COMPANY, London (GB)

(72) Inventors: Paul David Featonby, Northumberland (GB); Emanuele Ronchi, Cleveland (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 15/103,009

(22) PCT Filed: Dec. 18, 2014

(86) PCT No.: PCT/GB2014/053766
§ 371 (c)(1),
(2) Date: Jun. 9, 2016

(87) PCT Pub. No.: WO2015/097450
PCT Pub. Date: Jul. 2, 2015

(65) Prior Publication Data
US 2016/0313263 A1 Oct. 27, 2016

(30) Foreign Application Priority Data

Dec. 23, 2013 (GB) .................................. 1322945.5
Jan. 3, 2014 (GB) .................................. 1400102.8

(51) Int. Cl.
*G01N 23/08* (2006.01)
*G01N 23/18* (2006.01)
*G01N 23/04* (2006.01)

(52) U.S. Cl.
CPC ........... *G01N 23/08* (2013.01); *G01N 23/046* (2013.01); *G01N 23/18* (2013.01);
(Continued)

(58) Field of Classification Search
CPC ............ G01T 1/2985; G01N 2223/419; G01N 23/046; G01N 23/18; G01N 2223/628; G01N 23/08
See application file for complete search history.

(56) References Cited

U.S. PATENT DOCUMENTS

| | | |
|---|---|---|
| 4,338,521 A | 7/1982 | Shaw et al. |
| 5,614,720 A | 3/1997 | Morgan et al. |

(Continued)

FOREIGN PATENT DOCUMENTS

| | | |
|---|---|---|
| JP | 61274210 | 12/1986 |
| WO | 2005109346 | 11/2005 |
| WO | 2013064838 | 5/2013 |

OTHER PUBLICATIONS

International Search Report and Written Opinion of the International Searching Authority PCT/GB2014/053766 dated March 30, 2015.

(Continued)

*Primary Examiner* — Marcus Taningco
(74) *Attorney, Agent, or Firm* — Baker & Hostetler LLP

(57) ABSTRACT

A scanning method which is a method of identifying a change in the density of an object includes arranging a source of ionizing radiation and an array of radiation detectors Dn, where n is an integer from 1 to N, capable of detecting the radiation in such a way that radiation counts are counted by the detectors as the source and detectors are rotated around the object and normalized counts values are collated in a matrix such that a pattern may be detected within the matrix from which the presence of a change in the density of the object at a location lying on at least one of the radiation paths may be inferred.

14 Claims, 2 Drawing Sheets

(52) U.S. Cl.
CPC ............... *G01N 2223/1013* (2013.01); *G01N 2223/202* (2013.01); *G01N 2223/419* (2013.01); *G01N 2223/501* (2013.01); *G01N 2223/628* (2013.01); *G01N 2223/646* (2013.01)

(56) References Cited

U.S. PATENT DOCUMENTS

| | | | | |
|---|---|---|---|---|
| 6,925,145 | B2* | 8/2005 | Batzinger | G01N 23/18 378/4 |
| 6,934,354 | B2* | 8/2005 | Hoffman | A61B 6/032 378/149 |
| 7,329,875 | B2* | 2/2008 | McEvoy | G01T 1/2018 250/367 |
| 2004/0267114 | A1 | 12/2004 | Mundy et al. | |
| 2006/0078161 | A1 | 4/2006 | Schmiegel et al. | |
| 2008/0031400 | A1 | 2/2008 | Beaulieu et al. | |
| 2010/0303287 | A1 | 12/2010 | Morton | |
| 2011/0007956 | A1 | 1/2011 | Meyer et al. | |
| 2011/0274333 | A1 | 11/2011 | Prevrhal et al. | |
| 2013/0108007 | A1 | 5/2013 | Yin et al. | |
| 2016/0313261 | A1* | 10/2016 | Ronchi | G01N 23/046 |

OTHER PUBLICATIONS

United Kingdom Search Report dated Jun. 30, 2014; Application No. GB1322945.5.

United Kingdom Combined Search and Examination Report dated Mar. 30, 2015; Application No. GB1422659.1.

Rothbart et al., "Fast 2-D and 3-D Terahertz Imaging With a Quantum-Cascade Laser and a Scanning Mirror", IEEE Transaction on Terahertz Science and Technology, vol. 3, No. 5, Sep. 2013, pp. 617-624.

Hampel et al., "High resolution gamma ray tomography scanner for flow measurement and non-destructive testing applications", Review of Scientific Instruments, vol. 78, pp. 103704-9 (2007).

* cited by examiner

SCANNING METHOD

The present invention relates to a method of scanning a structure to detect changes in density by means of detecting radiation emitted by a radiation source by a radiation detector.

Methods of imaging objects and animals by X-ray tomography and positron-emission tomography are well-known, particularly in the field of medical imaging for diagnostic purposes. U.S. Pat. No. 4,338,521 describes an X-ray scanner for use in computerised tomography which has a detector comprising an array of detector modules, comprising a plurality of photodiodes and a plurality of scintillator crystals and a radiation beam collimator to direct collimated radiation to the scintillator crystals. A fan-shaped beam of x-rays from an x-ray source is directed through a patient to be detected by the detector. The source and detector are rotated around the patient to provide the data from which a tomographic image may be constructed. In positron-emission tomography (PET) a positron emitted by the decay of a radionuclide annihilates on contact with a suitable electron, causing the emission of two gamma photons of 511 keV in opposite directions. The detection of the direction of the gamma photons enables the estimation of the location of the annihilation event and thus the radionuclide within the patient. The PET scanner therefore incorporates an array of detectors which can detect gamma photons placed around the body of a patient. An image of the relative concentration of the radionuclide in the body may be constructed from the number of photons detected at each detector.

Whilst these scanning methods are well-developed and have become common for medical scanning, scanning a dense structure such as a pipeline presents difficulties because the density of the pipeline material is such that radiographic scanning must be done using gamma radiation which is of sufficient energy to penetrate and pass through the structure so that at least some radiation can be detected after the beam has passed through the structure. Gamma scanning of structures such as distillation columns is a standard industrial diagnostic method for measuring changes in density at different parts of the structure, for example to determine the location and integrity of column trays or other internal structures within the column. Normally this type of scanning is carried out with a single gamma source placed adjacent the column to emit a beam of radiation through the column and a radiation detector placed on an opposed part of the column to intersect and measure the radiation that has traversed the column between the source and detector. The source and detector are normally moved so that different parts of the column can be scanned. The use of many different positions and more than one source or detector can provide sufficient data for generating density maps, or tomographs, of the structure which is scanned, although the resolution is generally quite coarse. In order to generate higher resolution density maps, information from a much larger number of radiation paths through the structure must be used than is currently achieved with conventional column scanning methods.

The inspection of pipelines to find flaws such as wall loss, cracks or corrosion pitting is an application in which it would be desirable to use radiation scanning. A known problem for the oil and gas production industry is the inspection of pipelines located underwater, in particular on the sea-bed. Inspection of the interior of the pipeline by the use of pigs is not always possible, for example when the pipeline has varying diameter. Inspection from outside the pipe may be carried out by ultrasonic methods, although this is not suitable for pipelines having an insulation or coating. Gamma scanning can produce useful information about the density through a cross-section of the pipe. In order to produce information about the thickness of the walls of the pipe at sufficiently high resolution to identify small flaws that may be present in the walls of the pipe a large number of radiation paths through the pipe need to be scanned.

A particular method of scanning pipelines, is described in WO2013/064838. In that method a source of gamma radiation and an array of radiation detectors is rotated around a part to be scanned, such as a pipeline. The detector array is precisely arranged relative to the source so that the scanning can be carried out at high resolution. The scanning method of WO2013/064838 describes using scan data to construct a tomographic image. In order to further improve the scanning of pipelines and other objects, we provide an improved method of identifying discontinuities in the density of an object.

According to the invention, we provide a scanning method which is a method of identifying a change in the density of an object, said change representing a difference between the density of said object at a first location and the density of said object at a second location adjacent said first location, the method comprising the steps of:

a. arranging a source of ionizing radiation and an array of N radiation detectors Dn, where n is an integer from 1 to N, capable of detecting said radiation in such a way that
  i. radiation is emitted from the source in the direction of the array of radiation detectors,
  ii. radiation is emitted from the source towards any one of said radiation detectors along a radiation path, said radiation path being defined at each end by the source and the area of each detector facing said source;
  iii. up to N of said radiation paths may pass through said object; and
  iv. said source and said detector array are located in fixed positions relative to one another and movable along an arcuate scanning path around said object;
b. positioning the source and detector array at a known, position p0 on said scanning path;
c. acquiring count data Cnx from each detector Dn, for n=1 to N, for a predetermined period of time (the count period), said count data being related to the number of photons of radiation emitted by the source which have been detected by said detector during the count period;
d. repeating steps b and c at a plurality of different positions px on the scanning path, where x is an integer from 1 to X;
e. optionally adjusting each Cnx according to a calibration;
f. optionally converting each Cnx by means of a fan to parallel beam conversion algorithm to a converted Cnx;
g. For each detector Dn, calculating normalised Cnx values f for x=1 to X,
h. collating each normalised Cnx value in a matrix with rows and columns corresponding to n and x;
i. detecting a pattern within the matrix of normalised Cnx values which are higher or lower than the mean counts value;
j. and inferring from said pattern the presence of a change in the density of said object at a location lying on at least one of said radiation paths.

A scanning apparatus according to the invention comprises: a source of ionizing radiation and an array of N radiation detectors Dn, where n is an integer from 1 to N, capable of detecting said radiation, said source and detector array being arranged in such a way that
  i. radiation is emitted from the source in the direction of the array of radiation detectors,
  ii. radiation is emitted from the source towards any one of said radiation detectors along a radiation path, said radiation path being defined at each end by the source and the area of each detector facing said source;
  iii up to N of said radiation paths may pass through an object which is to be scanned; and
  iv. said source and said detector array are located in fixed positions relative to one another and movable along an arcuate scanning path around said object;
  means to position the source and detector array at a number of known, positions on said scanning path;
data processing means which is programmed to
  a. acquire count data Cnx from each detector Dn, for n=1 to N, for a predetermined period of time (the count period), said count data being related to the number of photons of radiation emitted by the source which have been detected by said detector during the count period at a plurality of different positions px on the scanning path, where x is an integer from 1 to X;
  b. optionally adjust each Cnx according to a calibration;
  c. optionally convert each Cnx by means of a fan to parallel beam conversion algorithm to a converted Cnx;
  d. For each detector Dn,
  e. calculate normalised Cnx values for x=1 to X, collate each normalised Cnx value in a matrix with rows and columns corresponding to n and x;
  f. and detect a pattern within the matrix of normalised Cnx values which are higher or lower than the mean counts value;

As the skilled person knows, the amount of electromagnetic radiation which passes from the source of radiation to a detector is directly related to the density and thickness of the material through which the radiation passes. When the thickness of material is constant, a more dense material attenuates the radiation more than a less dense material. Therefore the amount of radiation (indicated by the count of photons detected by the detector) reaching the detector is higher for less dense materials than for more dense materials.

Count data may represent a number of counts detected by the detector within a defined period of time, for example the count period. Count data may be expressed as count rates, i.e. the number of counts per period of time, e.g. counts per second.

Normalised Cnx values may be calculated by dividing Cnx by a Detector mean value of Cnx. The detector mean value of Cnx is the mean of all values of Cnx acquired by detector n. The mean value may be the arithmetic mean, i.e. the sum of all counts recorded by detector n at all positions from x=1 to X, divided by X. Alternatively a different mean value may be used for normalisation, for example mean of squares, sum of squares or log mean.

In addition to, or instead of, normalising the Cnx values for each detector n, the Cnx values may be normalised for each position x over all detectors. That means, for example, calculating the mean Cnx value detected by all detectors from n=1 to N at position x and then dividing all Cnx values for that position x by the calculated mean.

Normalisation of the Cnx data may be carried out by any other data normalisation method, The matrix of normalised count data may be displayed to an operator. By displaying the normalised count data in the form of a matrix, it is possible to observe patterns within the data from which discontinuities in the density of the object at a particular location may be inferred. When the matrix is displayed, it may be advantageous to represent the normalised count data in the matrix in the form of symbols. A symbol may be used to represent a selected range of normalised count data. Different symbols may represent different ranges of values within the normalised count data. Count data higher than the mean, indicating a material less dense than the mean density, may be represented by one or more different symbols. Count data less than the mean for any detector, indicating a material more dense than the mean density, may be represented by one or more different symbols. The symbols may take the form of coloured dots, pixels or blocks where each colour represents a selected range of normalised count data.

The matrix of count data may be analysed by pattern recognition algorithms using data processing software. In such a case, the location and characteristics of any discontinuities detected by analysis of any patterns found within the matrix of count data may be displayed to an operator.

Patterns within the normalised count data matrix indicate a change in the density of the object. This may indicate a defect within the object. For example when a pattern of normalised counts greater than the mean is found, indicating a less dense portion of the object, such a pattern may be caused by a loss of material through damage caused by corrosion, impact or other failure. When the object which is scanned is a pipeline for example, detection of such a discontinuity may enable the cause to be remedied before a failure of the pipeline occurs which can lead to leakage of contents from the pipeline. As another example, a pattern of normalised counts less than the mean indicates a more dense portion of the object. Such a pattern may be caused, for example, by a dense solid or semi-solid material filling a portion of a pipeline, which may reduce capacity for fluid flow through the pipeline.

A tomographic image may be constructed from the count data obtained from the detectors. A tomographic image is a representation of the shape and material characteristics (which may include the density) of the object. A tomographic image is convenient for the user to interpret because it is possible to indicate on the representation the size and location of any feature found in the tomography scan. Methods for constructing a tomographic image from a plurality of radiation count measurements are known to the person skilled in the art of radiation tomography and are not within the scope of this patent specification. A particular feature of the invention is the detection of a pattern within the matrix of normalised Cnx values which are higher or lower than the mean counts value. Whereas a change in density may appear as a pattern in the matrix using the method of the invention, the change, if small, may be more difficult to see in a tomographic image derived from the Cnx data.

The invention may be applied to a scanning method which is intended to produce a tomographic image. When the method of the invention is used and each normalised Cnx value is displayed in a matrix while the scanning operation is in progress, an operator of the process may, as a result of detecting a pattern in the matrix, decide that additional data is required in order to investigate the possibility that a discontinuity is present.

The count period may be varied according to the requirements of the method. The count period should be selected to allow a number of counts to be detected within the count period which is statistically distinguishable from "noise". The random error in the number of counts reduces as the number of counts increases. However, where the object is made from thick and/or dense materials, such as a pressure-resistant steel pipeline for example, the radiation from the source is highly attenuated by the object so that a relatively small number of photons penetrates the object to be detected by a detector. In such a case, in order to increase the number of photons detected, either the number or energy of photons emitted by the source must be increased (i.e. a larger or more energetic source is required) or the count period must be increased. The size or energy of the source may be constrained by safety considerations. The count period should not be so long as to make scanning of the object impractical. The count period may be less than a second. In an example, the count period may be selected to be within the range from 0.1 to 30 seconds.

The scanning path is arcuate. Normally the part of the object to be scanned lies wholly within the scanning path. The array of detectors is usually disposed in a plane parallel to the plane of the arcuate scanning path. The source and detector array therefore move along the scanning path so as to rotate around the object. Positions x lie on the scanning path and are angularly offset from one another. Positions x may be equally angularly spaced or the angular spacing between positions x may be different. The number of positions x at which count data is acquired affects the resolution of the scanning method and the precision at which a change in density may be located. In one embodiment, X may be 360 where each position is spaced at one degree of angle from adjacent positions on the scanning path and the scanning path is circular. For a circular scanning path it is preferred that X lies between 100 and 2000. For a circular scanning path it is preferred that X lies between 180 and 1450.

The method may be carried out by acquiring data from the detectors as the source and detector move along the scanning path. The movement of the source and detectors may lie within a plane parallel to the plane of the detector array. Data may be acquired from the detectors continually and recorded together with a record of the position at which the data was acquired. The positions of data collection may then be banded into a series of angular intervals related to the start position p0. Such angular intervals may be regular angular intervals. The angular intervals may be selected to be separated by at least a degree or less than a degree. For example, a continuous acquisition of data may be banded into angular intervals of half or one degree or a quarter of one degree. When the source and detector array are moved through a complete circle and the count data is banded into intervals of one quarter of a degree, X is 1440. The speed of movement of source and detector and the angular interval between positions x affects the count period. In a working embodiment of the invention for scanning steel pipeline we have found that a circular scanning path may be completed in 60 minutes or less. When the count data is banded into angular intervals of one quarter degree, the effective count period is 2.5 seconds. The speed of movement along the scanning path may be constant.

In such a method the source and detector array are moved continuously along the scanning path and count data is acquired continuously from each detector until the scan has been completed. In such a method the steps c d become:
  c. acquiring count data Cnx from each detector Dn, for n=1 to N, for a predetermined period of time (the count period), said count data being related to the number of photons of radiation emitted by the source which have been detected by said detector during the count period, whilst moving said source and detector array along the scanning path;
  d. banding the count data into count data acquired at a plurality of different angular positions px on the scanning path, where x is an integer from 1 to X;

The number of detectors N may be greater than 20 and may be greater than 50. The number of detectors which acquire count data may affect the resolution of the scanning method, the time taken to complete a scan and the precision at which a change in density may be located.

The count data Cnx may be adjusted according to a calibration. In one embodiment of the method a calibration may be carried out by acquiring count data Cnx at each position x in the presence of a known object of consistent density. The known "object" may comprise air or water, which fills the space between the source and detector. Calibration count data may be stored in a data processor memory. The calibration adjustment may be made by subtracting or dividing the calibration count data (or a derivative of the count data) from the count data acquired during the scanning method.

The counts data Cnx may be converted to converted counts data by means of a fan to parallel beam conversion algorithm. The use of fan to parallel beam conversion is known in the field of radiation tomography where measurements are carried out using a radiation beam which is fan-shaped, originating from a small or point source. Suitable fan to parallel beam conversion algorithms are available to the skilled person. Such a conversion may assist in locating the position of a change in density from the count data matrix. The conversion is, however, optional because it does not usually affect the presence of a pattern in the count data matrix. The conversion may correct a distortion of the position within the matrix of such a pattern.

The method may include a step of calibrating the detectors. This step may be carried out in the absence of the object to be scanned. Preferably the calibration step is carried out in the same or substantially the same environmental conditions as will be used for the scan. For example, when the method is used to scan a subsea pipeline, the calibration may be carried out near the pipeline so that seawater of similar pressure, temperature and salinity is present between the source and detector as will be present during the scan. The calibration step may include obtaining an energy spectrum scan for each detector in the array. The information from the energy spectrum scan may be used to identify suitable energy windows within which to count photons detected by the detector. A broken or defective detector may also be identified from its energy spectrum.

The scanning apparatus may comprise a pipe-scanning apparatus of the type described in WO2013/064838. Alternatively the scanning apparatus may comprise a different apparatus in which radiation is used to estimate the density along a path through an object or structure.

In a typical scanning apparatus, the source may be housed in a source unit comprising a source of penetrating radiation, a source-holder and a collimator. The collimator and source-holder may be combined. The collimator is formed of a material which is highly attenuating to the radiation emitted by the source and is normally formed of a heavy alloy material of the type known and commonly used for shielding radiation of the appropriate energy and type. The collimator is located and adapted to limit the radiation emitted by the source unit to a predetermined beam shape and direction. Preferably the radiation beam is shaped by the collimator to form a fan, cone, frusto-cone, or sector in each case having the source as origin. A preferred beam shape is a cylindrical sector, i.e. a sector having a thickness rather than being planar. Preferably the beam is collimated to provide a beam area at the location of the detector(s) which has the same general shape and area as the combined detecting surface(s) of the array of detectors. The source unit may be mounted on a support.

The radiation source is selected by the transparency to the radiation of the material(s) to be measured, e.g. a vessel and/or its contents (i.e. the attenuation coefficient of the medium) and the availability of suitable sources and detectors. For scanning large solid structures such as process vessels and pipelines, suitable sources of gamma include $^{60}Co$ and $^{137}Cs$, $^{133}Ba$, $^{241}Am$, $^{24}Na$ and $^{182}Ta$, however any gamma-emitting isotope of sufficient penetrating power could be used, and many such are already routinely used in density gauges, such as those used as level measurement devices. Usually, the half-life of the radioisotope used will be at least 2, and desirably at least 10, years. The half-lives of the radioisotopes mentioned above are: $^{137}Cs$ gamma about 30 years, $^{133}Ba$ about 10 years and $^{241}Am$ about 430 years. Suitable sources generally emit radiation at energies between about 40 and 1500 keV.

The source unit may include one or more than one source. The scanning method may utilise more than one source unit if required.

The scanning apparatus may comprise an array of radiation detectors. For example the scanning unit may comprise an array of at least 10 detectors. The detector, or each of the detectors, may comprise a scintillator, normally supported in a suitable position so that a surface thereof, which may be referred to as the detecting surface, intersects a path of radiation emitted by the source at a particular distance from and a particular angle to the radiation source. The detector or each detector of a detector array may be housed within a collimator which reduces the detection of radiation impinging on the detector from an angle outside the angle of a linear radiation path from the source. The collimator comprises a material which is impermeable to the radiation emitted by the source. The collimator may cover a part of the detecting surface of the detector to delimit the portion of the detecting surface on which radiation may impinge.

When the detector unit comprises more than one detector, deployed in the form of an array of detectors, a preferred embodiment of the invention comprises a block of shielding material (a "detector block") having openings extending inwardly from a surface of the block, each opening containing a detector, the detecting surface being accessible to radiation from outside the block. A portion of the detecting surface may be covered by shielding material for the purposes of delimiting the area of the detecting surface or for mechanically retaining the detector within the opening. The non-detecting surfaces of the detector may optionally be enclosed partially or wholly within the opening and covered by the shielding material. The detector block includes means by which the collecting surface of the scintillator(s) may be brought into contact with a photodetector or a light transmitter. Such means may take the form of an open passage through which the scintillator extends so that the collecting surface is accessible to the photodetector or light transmitter.

When the detector comprises a scintillation material, such as a scintillation crystal or a polymeric scintillator, a photodetector is provided which is optically coupled to the scintillator in order to detect and measure light generated by the scintillator in response to photons of radiation from the source. The photodetector may be a photodiode, photomultiplier tube (PMT), a silicon photomultiplier or other suitable light detecting device. The photodetector generates an electrical signal in response to light entering it through an optical window. The wavelengths detected by the photodetector should be matched as far as possible to the wavelengths generated by the scintillator to maximise the detection efficiency. Normally a photodetector is provided for each scintillator so that the amount of radiation detected by each scintillator can be measured independently of the other scintillators.

Each detecting surface preferably forms a tangent to an arc of a circle having a radiation source as its origin. In one embodiment, each detector surface forms a tangent to the surface of a part of a sphere having the radiation source as its origin.

Other forms of radiation detector may be employed in a scanning apparatus of the invention. For example, Geiger-Müller tubes or other detectors may be used.

The apparatus further comprises a signal/data processor for operating on the electrical signal from the detectors in the detector unit(s) and a controller to control the operation of the apparatus. Signals representative of the counts of photons detected by the scintillators are processed by the data processor. The signal may be subjected to smoothing or stabilisation algorithms, averaged or otherwise operated on according to standard practices. A data processor may perform calculations based on the signal from the radiation detector or from a signal processor if present. The data processor may output information concerning the amount of radiation measured over a time interval, or it may further calculate derived properties of the scanned structure, usually in the form of a bulk density or a change in bulk density between radiation paths through the structure. The scanning method is carried out at a plurality of radially offset positions around the structure so that density data may be acquired at a variety of angles through the structure and a tomography algorithm may be used to provide information about the changes in density at different paths through the structure. In a preferred form the data from the detectors is operated on by the data processing unit using tomography algorithms in order to produce a graphical representation of the density or composition of the structure along different paths. The data processor may contain a calibration or information concerning the radiation source. The data processor output is may be connected a display or a (optionally wireless) transmission means so that a signal can be sent from the apparatus to a remote location. Alternatively a signal comprising data from the radiation detector itself may be sent, for processing at a remote location. A power supply is provided to power the photodetectors, data processor and control electronics and also to power motors for moving the apparatus. Movement of the scanning apparatus, for example to open and close the apparatus and to rotate the source and detector, may be accomplished by means of electrically or hydraulically powered motors or actuators The apparatus may be moved between different locations or orientations with respect to the structure where the method of the invention is repeated. In this way a record of the attenuation to radiation through each radiation path through the structure may be gathered and used to calculate the location of changes or to build a representation of the structure and its contents.

An example incorporating several optional features of the invention will be described with reference to the appended drawings.

Figure 2:
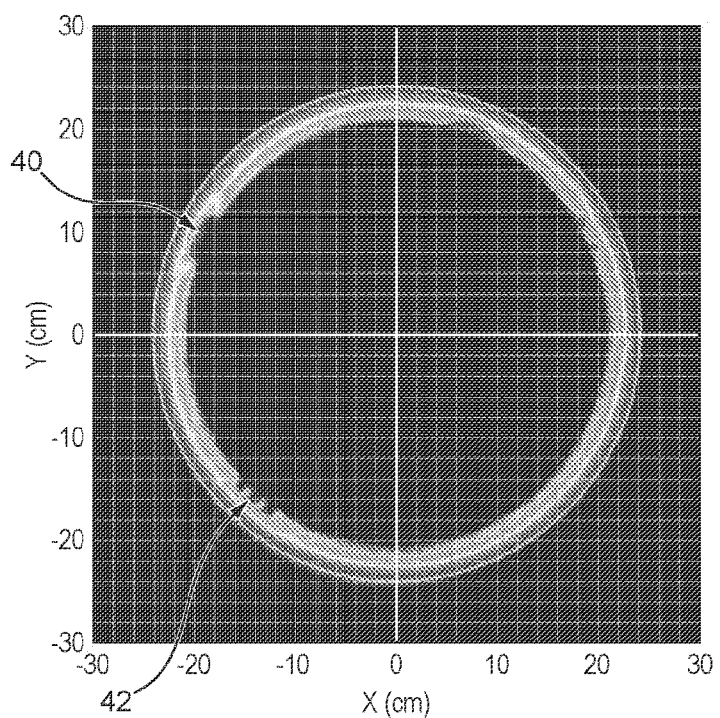
FIG. 2 is a tomographic image of the pipe.
Figure 3:
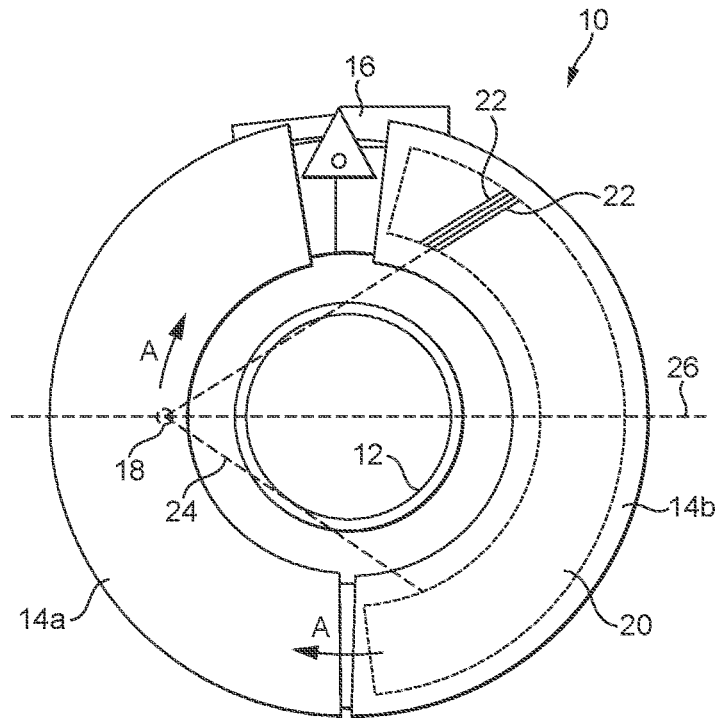
FIG. 3 is a schematic view of a section of a pipe enclosed within a scanning apparatus of the invention.

FIG. 3 shows a pipe scanning apparatus 10 surrounding a pipeline 12 (shown in section). The scanning apparatus comprises a pair of hinged housings 14a & 14b which open and close by means of hydraulic apparatus 16. When the housings are open the apparatus may be moved around the pipe to be scanned and then closed around it. A source of gamma radiation 18 is located within housing 14a together with collimation and shielding to emit a collimated cone of radiation towards the detector array 20. An arcuate array 20 of 95 radiation detectors 22 (only two of which are shown, for illustration purposes) is located in housing 14b. The detectors comprise scintillation crystals, each coupled to a photodetector. The source and the detector array are fixed in relation to each other but are rotatable around the pipeline. The direction of rotation is shown in this example by arrows A. The direction of rotation is not, however, critical. The rotation path lies within the plane of the detector array. Each detector of the detector array detects radiation from the source which has passed along a portion of a cone-shaped path between the source and the detector. A number of radiation paths may be defined, each radiation path being between the source and each detector in the detector array. Each detector is directed towards the source and set within collimation and shielding materials to minimise its detection of scattered radiation. When a radiation path intersects the pipe, as shown, for example, by the dashed line 24, the radiation is attenuated by the material of the pipe wall so that the radiation detected by a radiation detector in that path is less than the radiation detected by a detector located in a path which intersects less of the pipe material. In that way, information can be collected about the density of material along each radiation path and, by means of the rotation of the source and detector array and using a tomography algorithm, an image of the pipeline wall thickness may be assembled. Such an image is shown in FIG. 2.

Figure 1:
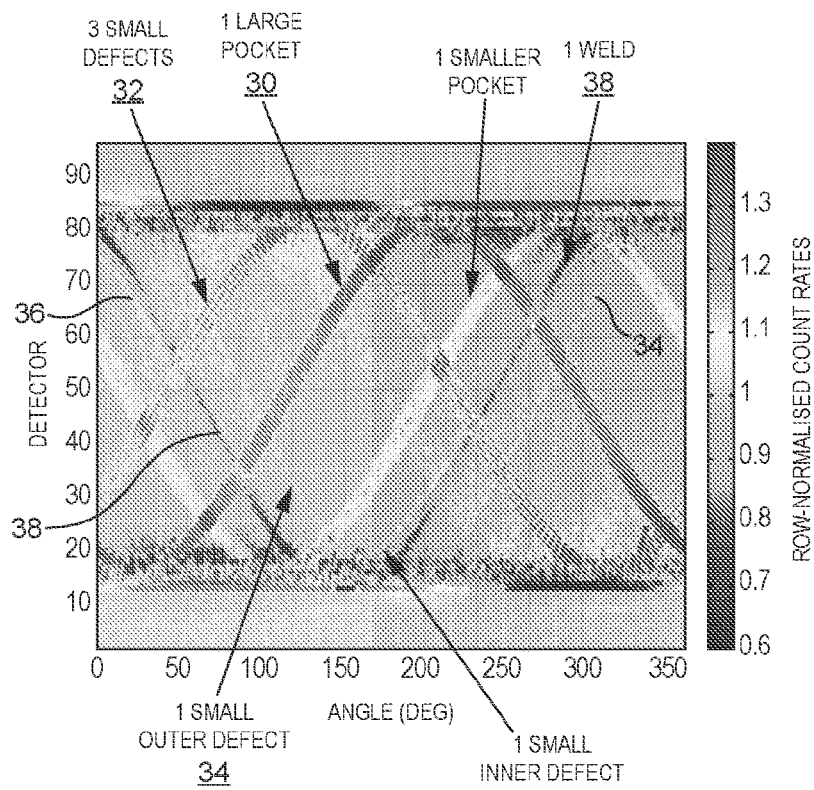
FIG. 1 is a coloured matrix of counts arranged by angle and detector number, from a scan of a pipe according to the method of the invention.

FIG. 1 shows a representation of a coloured matrix of individual detector number n (rows) and angle of source to the pipeline (columns). It will be appreciated that the coloured matrix represented as grey-scale in FIG. 1 may lose some detail from its original coloured form. The row-normalised count rates are represented by a coloured scale where, in this example, values less than 1 are shown in a blue colour and values greater than 1 are yellow (which show in the Figure as a light grey-white) and red. Values of 1±about 0.075 display in green, which is a mid-grey in the Figure. Count rates are number of counts per unit time, where unit time may be expressed in seconds or as the count period if all count periods are of equal duration.

Figure 4:
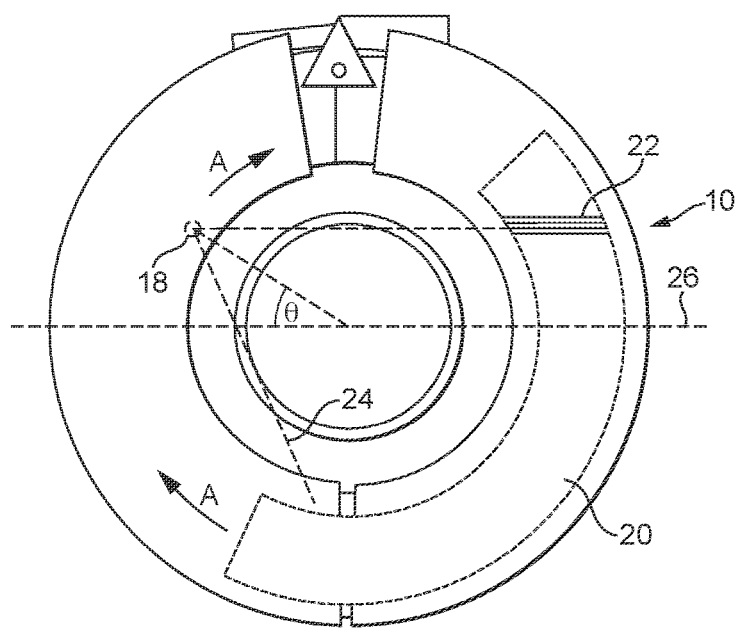
FIG. 4 is a schematic view of a section of a pipe enclosed within a scanning apparatus of the invention.

In the method of the invention, with the source and detector array positioned at a start position, which is designated as 0° of angle, data is collected from each of the 95 detectors representing the number of counts of radiation received during a count period of 10 seconds. The source and detector are then rotated with respect to the pipe to a second position at a different angle and counts data is collected from each detector at that second position. FIG. 4 shows schematically the arrangement described in FIG. 3 in which the source and detector array have been moved rotationally with respect to pipe 12 to a new position in which the source is angled at angle θ to the horizontal (indicated by dashed line 26). In this example, data is collected at 1 degree increments of rotation. In this example, following a calibration adjustment to account for small differences between the detectors, a fan-to-parallel beam adjustment algorithm is applied to the data. For each detector, a mean counts value is calculated as the mean of all of the counts detected at each position—i.e. the total number of counts divided by the number of positions at which counts data is acquired. A normalised count rate can then be calculated for each detector at each position. Referring to FIG. 1 each row of the matrix shows, for a single detector, the normalised count rate, i.e. the deviations from the mean counts, detected at each angular position.

FIG. 1 clearly shows several sinusoidal patterns in the data. A single discontinuity in the density of the pipe material causes a sinusoidal variation in the data because each detector detects the same discontinuity at a different angular position. Large discontinuities, such as a large "pocket" in the thickness of the pipe wall are shown as wide patterns e.g. line 30 on FIG. 1, of count rates which are higher than the mean count rate. This line would show as red on the original coloured matrix. The pocket causing such a response is also clearly visible at 40 on the tomographic image of FIG. 2. Three smaller pipe wall defects show clearly as pattern 32 on FIG. 1 and in FIG. 2 at 42. A pattern of higher than mean counts 38 indicates the position of a weld in the pipe at which the weld material is more dense than the pipe wall. Other patterns 34, 36 which are visible on the matrix of FIG. 1 are much harder to see on a tomographic image. The patterns 34, 36 of the matrix in FIG. 1 enable an operator to identify such smaller discontinuities and decide whether it is necessary to re-scan that part of the pipeline or merely record a small defect existing at the location indicated. In the absence of the matrix, it is possible that such defects would not be identified in the scan from the tomographic image alone.

The invention claimed is:

1. A scanning method which is a method of identifying a change in the density of a pipeline located underwater, said change representing a difference between the density of said pipeline at a first location and the density of said pipeline at a second location adjacent said first location, the method comprising the steps of:
   a. arranging a source of ionizing radiation and an array of N radiation detectors Dn,
   where n is an integer from 1 to N, capable of detecting said radiation in such a way
   that
      i. radiation is emitted from the source in the direction of the array of radiation detectors,
      ii. radiation is emitted from the source towards any one of said radiation detectors along a radiation path, said radiation path being defined at each end by the source and the area of each detector facing said source;
      iii. up to N of said radiation paths may pass through said pipeline; and
      iv. said source and said detector array are located in fixed positions relative to one another and movable along an arcuate scanning path around said pipeline;
   b. positioning the source and detector array at a known, position p0 on said scanning path;
   c. acquiring count data Cnx from each detector Dn, for n=1 to N, for a predetermined period of time, said count data being related to the number of photons of radiation emitted by the source which have been detected by said detector during the predetermined period of time;

d. repeating steps b and c at a plurality of different positions px on the scanning path, where x is an integer from 1 to X;
e. optionally adjusting each Cnx according to a calibration;
f. optionally converting each Cnx by means of a fan to parallel beam conversion algorithm to a converted Cnx;
g. for each detector Dn, calculating normalised Cnx values for each Cnx for n=1 to N and for x=1 to X,
h. collating each normalised Cnx value in a matrix with rows and columns corresponding to n and x;
i. analyzing the matrix to detect a pattern within the matrix of normalised Cnx values which are higher or lower than the mean counts value; and
inferring from said pattern the presence of a change in the density of said pipeline at a location lying on at least one of said radiation paths.

2. A scanning method according to claim 1, wherein said matrix of normalised count data is displayed to an operator.

3. A scanning method according to claim 2, wherein the normalised count data is represented in the matrix in the form of symbols.

4. A scanning method according to claim 3, wherein the symbols take the form of coloured dots, pixels or blocks where each colour represents a selected range of normalised count data.

5. A scanning method according to claim 1, wherein the matrix of count data is analysed by pattern recognition algorithms using data processing software.

6. A scanning method according to claim 1, wherein a tomographic image is constructed from the count data obtained from the detectors.

7. A scanning method according to claim 1, wherein the detection of a pattern in the matrix causes additional count data to be acquired.

8. A scanning method according to claim 1, wherein the pipeline, or a portion thereof, lies wholly within the scanning path.

9. A scanning method according to claim 1, wherein positions x are equally angularly spaced.

10. A scanning method according to claim 1, wherein X lies between 180 and 1450.

11. A scanning method according to claim 1, wherein data is acquired from the detectors as the source and detector move along the scanning path.

12. A scanning method according to claim 1, wherein data is acquired from the detectors continually and recorded together with a record of the position at which the data was acquired.

13. A scanning method according to claim 11, wherein the positions of data collection are banded into a series of angular intervals related to the start position p0.

14. A scanning apparatus for identifying a change in the density of a pipeline located underwater, the scanning apparatus comprising a source of ionizing radiation, an array of N radiation detectors Dn, where n is an integer from 1 to N, capable of detecting said radiation, said source and detector array being arranged in such a way that
   i. radiation is emitted from the source in the direction of the array of radiation detectors,
   ii. radiation is emitted from the source towards any one of said radiation detectors along a radiation path, said radiation path being defined at each end by the source and the area of each detector facing said source;
   iii. up to N of said radiation paths may pass through pipeline which is to be scanned; and
   iv. said source and said detector array are located in fixed positions relative to one another and movable along an arcuate scanning path around said pipeline;
   means to position the source and detector array at a number of known, positions on said scanning path; data processing means which is programmed to
   a. acquire count data Cnx from each detector Dn, for n=1 to N, for a predetermined period of time, said count data being related to the number of photons of radiation emitted by the source which have been detected by said detector during the predetermined period of time at a plurality of different positions px on the scanning path, where x is an integer from 1 to X;
   b. optionally adjust each Cnx according to a calibration;
   c. optionally convert each Cnx by means of a fan to parallel beam conversion algorithm to a converted Cnx;
   for each detector Dn,
   d. calculate normalised Cnx values for each Cnx for n=1 to N and for x=1 to X;
   e. collate each normalised Cnx value in a matrix with rows and columns corresponding to n and x; and
   analyze the matrix to detect a pattern within the matrix of normalized Cnx values which are higher or lower than a mean counts value.

* * * * *